United States Patent [19]
Knapps

[11] Patent Number: 4,724,829
[45] Date of Patent: Feb. 16, 1988

[54] ANATOMICAL AID

[76] Inventor: Oliver L. Knapps, 5337 Edgewater Rd., Newark, Calif. 94560

[21] Appl. No.: 857,639

[22] Filed: Apr. 29, 1986

[51] Int. Cl.[4] .............................................. A61F 5/41
[52] U.S. Cl. .................................................... 128/79
[58] Field of Search ......................................... 128/79

[56] References Cited

U.S. PATENT DOCUMENTS

| | | |
|---|---|---|
| 765,261 | 7/1904 | Wise ..................................... 128/79 |
| 1,216,099 | 2/1917 | Falck .................................... 128/79 |
| 1,511,572 | 10/1924 | Marshall ............................... 128/79 |
| 2,868,192 | 1/1959 | Dannen ................................. 128/79 |
| 3,397,689 | 8/1968 | Marcantonio ......................... 128/79 |
| 3,455,301 | 7/1969 | Clark .................................... 128/79 |
| 3,461,863 | 8/1969 | Sullinger .............................. 128/79 |
| 3,495,589 | 2/1970 | Clement ................................ 128/79 |
| 3,621,840 | 11/1971 | Macchioni ............................ 128/79 |
| 3,636,948 | 1/1972 | Atchley ................................ 128/79 |
| 3,820,533 | 6/1974 | Jones .................................... 128/79 |
| 4,022,196 | 5/1977 | Clinton ................................. 128/79 |
| 4,240,413 | 12/1980 | Hanus ................................... 128/79 |
| 4,381,000 | 4/1983 | Duncan ................................. 128/79 |
| 4,429,689 | 2/1984 | Yanong ................................. 128/79 |
| 4,440,183 | 4/1984 | Miller ................................... 128/79 |
| 4,539,980 | 9/1985 | Chaney ................................. 128/79 |

FOREIGN PATENT DOCUMENTS

| | | |
|---|---|---|
| 260938 | 1/1912 | Fed. Rep. of Germany ........ 128/79 |
| 491522 | 8/1927 | Fed. Rep. of Germany ........ 128/79 |
| 2460812 | 7/1976 | Fed. Rep. of Germany ........ 128/79 |

Primary Examiner—Robert Peshock
Assistant Examiner—Cary E. Stone
Attorney, Agent, or Firm—Robert R. Tipton

[57] ABSTRACT

A compression assembly is used to maintain engorgement of the penis and comprises a generally cylindrical compression member having one end adapted to engage and compress perpendicularly against the pubic region proximate the base of the engorged penis.

5 Claims, 5 Drawing Figures

ANATOMICAL AID

BACKGROUND OF THE PRIOR ART

This invention relates generally to devices for relieving male impotence and in particular, for maintaining engorgement of the penis.

It is well known from medical and popular literature that impotence of the human male is a common occurrence, where, for various reasons, it is difficult to attain or maintain an erection of the penis.

Although impotence can occur at any age, it is more commonly found in older males.

For the normal healthy male, blood flows into the penis through the profunda and dorsal arteries. Blood circulates through the penis and leaves by way of the deep dorsal and subcutaneous veins.

The deep dorsal vein lies subfascially in the midline of the penis between the dorsal arteries passing out of the base of the penis through the arcuate pubic and transverse perineal ligaments where it divides into left and right veins to join the prostatic plexus.

The subcutaneous veins collect blood subcutaneously from the penis and conduct it to the external pudendal vein.

The erection process involves, basically, the engorgement of the venous sinuses of the corpus cavernosa with blood from the profunda arteries and the engorgement of the venous sinuses of the corpus spongeosum with blood from the dorsal arteries.

The erection is maintained by restriction of the flow of blood out of the penis through the subcutaneous dorsal vein and the deep dorsal vein.

The point along the veins where flow is naturally restricted lies below the base of the penis.

All of the devices of the prior art in one way or another attempted to restrict the flow of blood out of the penis by applying radial pressure to the shaft of the penis either in the form of a tourniquet about the penis or pressure devices that apply pressure directly to various areas radially proximate the base of the penis.

One device utilized a central elastic ring having elastic loops attached to opposite sides of the ring. The loops were of sufficient size to insert the fingers on opposite hands into the loops whereupon, when the hands are spread away from each other, the elastic ring was enlarged for being set on the root of a penis. When released, the ring acted as a check valve to enable blood to be massaged into the penis and to prevent its outflow to thereby maintain engorgement of the penis.

A different device utilized a resilient band having a plurality of radially extending projections on the inner surface thereof. When wrapped tightly around the penis near its base, these radial inward projections were effective to restrict the flow of blood from the penis to maintain engorgement thereof.

A further device of the prior art utilized an annular sleeve fabricated from an elastic material. The sleeve was adapted to receive and snugly engage the base of the male organ with a compressive fit. The base of the sleeve was adapted to apply pressure to the subcutaneous veins of the male organ in order to restrict the flow of blood therefrom. The sole feature of the device was to apply radial pressure to the penis to restrict the flow of blood.

Still another device of the prior art utilized an elastic tubular element which fitted around the base of the penis. The bore of the tubular element had a diameter corresponding to the mean diameter of the penis in a non-engorged state. A radial slit was provided in the tubular element. An elastic ring was placed around the outside of the tubular element whereby, as engorgement occurs, the tubular element was allowed to expand, however, applying radial pressure to the penis to restrict the flow of blood as determined by the elasticity of the elastic ring.

Still a further device of the prior art utilized a highly stretchable rubber tube. The tube acted in the manner of a tourniquet in which a bight was maintained in the stretchable tube by passing the tube through apertures in a connecting tube stretch located on the opposite side of tube and spaced lengthwise of the tube.

All of these devices of the prior art presented certain dangers in restricting the flow of blood to and from the tissues of the penis if left too long in place. In some cases, the use of the particular device would not be without pain and discomfort.

SUMMARY OF THE INVENTION

The anatomical aid device of the present invention does not apply pressure radially to the penis but rather it applies a gentle pressure perpendicular to the pubic region immediately adjacent the base of the penis. By application of pressure to this area, pressure is also applied to the deep dorsal vein and subcutaneous veins below the base of the penis in order to maintain engorgement thereof.

The device of the present invention comprises, basically, a generally cylindrical compression member having one end adapted to engage and compress perpendicularly against the body pubic region proximate the base of the penis, the inside diameter of the cylindrical compression member being greater than the outside diameter of the penis when engorged. A pair of straps are connected to the cylindrical compression member proximate the end thereof distal the end adapted to engage and compress against the pubic region. The straps, respectively, pass around the right and left sides of the users body and between the legs in order to maintain compression of the cylindrical member against the pubic region. The device also comprises means fabricated from a flexible material attached, respectively, to each of the straps proximate the cylindrical compression member to define a suspensory pouch. The suspensory pouch is adapted to hold the testes close to the body of the user.

It is, therefore, an object of the present invention to provide a device for maintaining engorgement of the penis during coitus.

It is a further object of the present invention to provide a device for maintaining the engorgement of the penis by applying annular pressure perpendicular to the pubic region proximate the base of the penis.

It is a further object of the present invention to provide a device for maintaining engorgement of the penis utilizing a cylindrical compression member having an inside diameter greater than the outside diameter of the engorged penis.

These and other objects of the present invention will become manifest upon study of the following detailed description when taken together with the drawings.

DESCRIPTION OF THE PREFERRED EMBODIMENT

Figure 1:
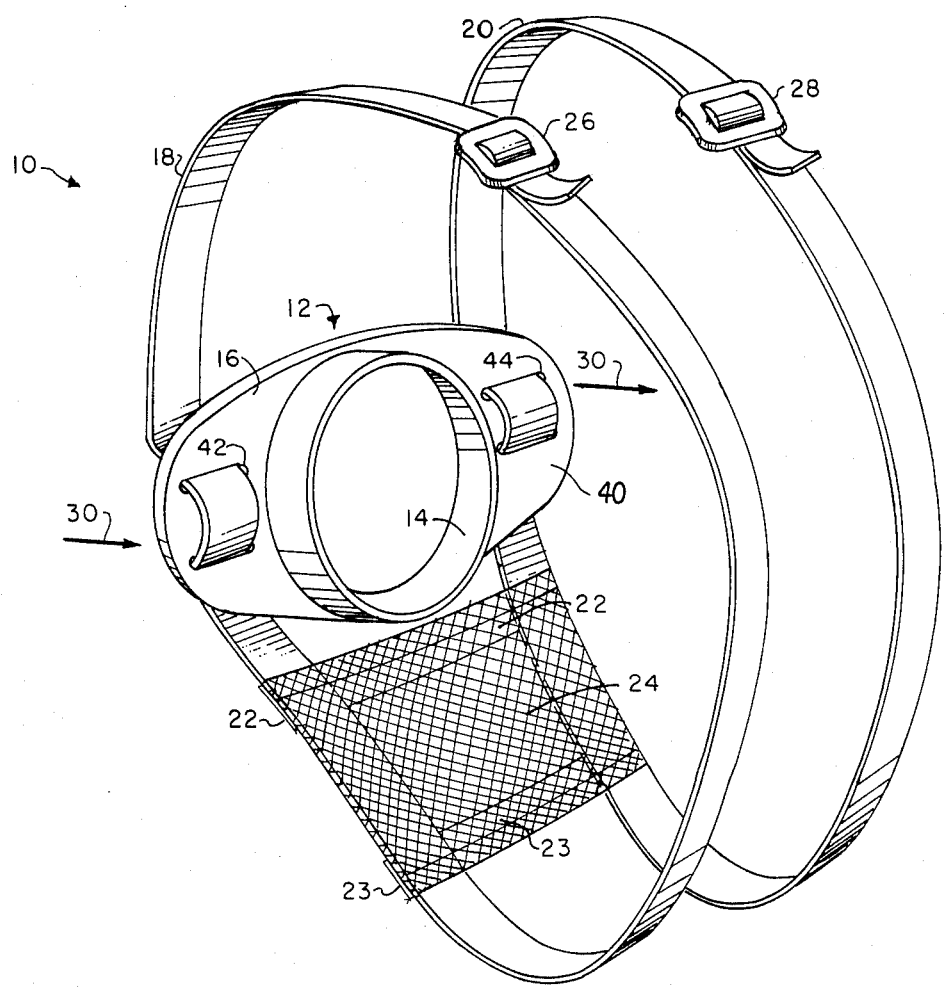
FIG. 1 is an isometric view of the anatomical aid device of the present invention.

With reference to FIG. 1, there is illustrated an isometric view of the anatomical aid device 10 of the present invention comprising, basically, compression assembly 12 having a generally cylindrical compression member 14 and base support 16 connected on its left and right side, respectively, to left body strap 18 and right body strap 20 (taken with reference to the body of the user).

A pair of elastic spacer straps 22 and 23, having each end respectively attached to left and right body straps 18 and 20, is disposed below compression assemble 12, and holds left and right straps 18 and 20 together where they pass through the crotch of the user.

A suspensory pouch 24, fabricated from a flexible material, such as an open weave fabric, is also attached to left and right body straps 18 and 20 proximate spacer straps 22 and 23. Suspensory pouch 24 is adapted to hold the testes of the user close to his body to provide both warmth and stimulation.

Spacer straps 22 and 23 can be either separate straps fabricated from an elastic material so as to conform around the body parts or they can be elastic material woven into the mesh material of suspensory pouch 24 with seam/slots along the top and bottom edge or selvage of suspensory pouch 24.

A buckle 26 in left body strap 18 and a buckle 28 in right body strap 20 are used to adjust the tension in straps 18 and 20 for various body shapes and sizes.

Anatomical aid 10 is placed on the body with compression assembly 12 facing toward the pubic region of body in the direction of arrows 30 with the penis passing through cylindrical compression member 14. For clarity, compression assembly 12 in FIG. 1 is shown without any insert in cylindrical compression member 14.

With reference to FIGS. 2, 3, 4 and 5, there is illustrated both plan and cross-sectional views of the compression assembly 12 of the present invention.

Although anatomical aid 10 can be used solely as shown in FIG. 1, it may be desirable to allow for anthropometric variations in diameter of the engorged penis among the male population generally. For this reason, FIGS. 2 through 5, inclusive, include a means for providing for these anthropometric variations in size of the penis among the general population.

Figure 2:
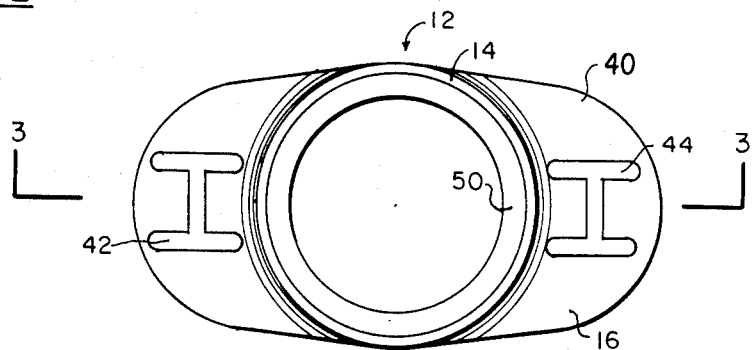
FIG. 2 is a plan view of the compression assembly of the anatomical aid device of the present invention and means for connecting it to a pair of body straps.
Figure 3:
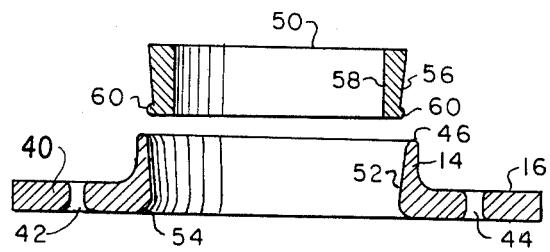
FIG. 3 is a cross-sectional, elevational exploded view of the anatomical aid device of the present invention showing the compression assembly and insert of FIG. 2 taken at lines 3—3.

FIG. 2 is a plan view of compression assembly 12 while FIG. 3 is an exploded view of compression assembly 12.

Compression assembly 12 comprises a generally planar base support member 40 having left and right strap fastening "I" slots 42 and 44, respectively, on the left and right sides thereof, and a generally cylindrical compression member 14 projecting upwardly therefrom toward the body of the user and terminating in a top rim 46.

Top rim 46 is provided with a rounded edge and is adapted to engage and compress perpendicularly against the pubic region of the user proximate the base of the penis.

To allow for variations in anthropometric variations in the sizes of body parts, an insert 50 having a predetermined fixed inside diameter is provided to be inserted in cylindrical compression member 14.

Figure 4:
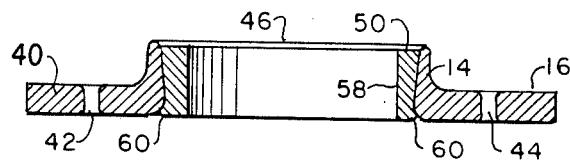
FIG. 4 is a cross-section of a typical assembled anatomical aid device of the present invention showing the manner in which the insert is retained in the compression assembly.

FIG. 3 is an exploded view of insert 50 and compression member 14, while FIG. 4 is an assembled view of insert 50 and compression member 14.

To accommodate insert 50, the inside diameter 52 of generally cylindrical compression member 14 is tapered to define a frusto-conical shape with a rounded edge 54 proximate the narrowest portion (distal rim 46) where it is formed into generally planar base support 16.

The outside diameter 56 of generally cylindrical insert 50 is also tapered to define a frusto-conical shape adapted to mate with the inside surface of generally cylindrical compression member 14.

The inside diameter 58 of cylindrical insert 50 can be vary. The fixed inside diameter of any particular insert will depend upon the diameter of the engorged penis of the user. The preferred inside diameter of insert 50 (or cylindrical compression member 14 is used without any insert) is one that will not provide any radial compression of the penis shaft above its base but will provide compression perpendicular to the pubic region of the body immediately adjacent and as close as possible to the base of the penis.

As distinguished from the devices of the prior art, the anatomical device 10 of the present invention does not directly compress the exposed shaft of the penis radially.

The inside diameter of three typical inserts (or cylindrical compression member 14 if used without an insert) is as follows:

TABLE 1

| Item | Diameter | Size |
| --- | --- | --- |
| Compression Member 14 | 1.625 inches | Extra Large |
| Insert A | 1.500 inches | Large (average) |
| Insert B | 1.444 inches | Medium |
| Insert C | 1.385 inches | Small |

To hold cylindrical insert 50 in engagement with the inside surface 52 of generally cylindrical compression member 14, a peripheral detent or raised portion 60 is provided about the base of outside surface 56 of insert 50.

Figure 5:
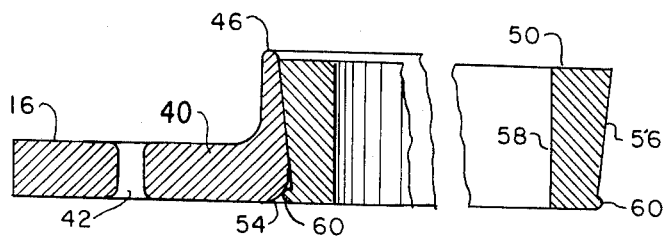
FIG. 5 is an enlarged partial section of FIG. 4 showing the details of the insert member and its manner of installation in the cylindrical compression member.

Detent or raised portion 60 is adapted to engage rounded portion 54, as can be seen in FIG. 5.

The height of insert 50 is preferably established to be less that the height of cylindrical compression member 14 in order to allow lip or rim 46 of cylindrical compression member 14 to engage and compress against the pubic region proximate the base of the penis.

Typically the height of generally cylindrical compression member 14 is about 0.500 inches while the height on insert 50 is about 0.453 inches.

To use anatomical aid 10 of the present invention, the left and right strap loops 18 and 20, as shown in FIG. 1, are spread laterally apart and the left and right legs of the user are put through the respective left and right body strap loops 18 and 20.

The aid device 10 is then pulled up by straps 18 and 20 to the hip level and the penis placed through cylindrical compression member 14 and any insert 50 it might contain.

Compression assembly 12 is adjusted along straps 18 and 20 so that suspensory pouch 22 comfortably contains and holds the testes of the user.

Straps 18 and 20 are next pulled over the hips with the straps passing through the crotch and between the buttocks of the user. Final adjustments can then be made so as to hold cylindrical compression member 14 firmly against the body pubic region.

Although the preferred embodiment has been described in detail, the description is not intended to limit the scope of this invention but to allow variations limited only by the claims which follow.

I claim:

1. A device for maintaining engorgement of the human penis comprising
    a generally cylindrical main compression member comprising
    a main compression member inside surface,
    a main compression member outside surface,
    a top rim adapted to engage and compress perpendicularly against the pubic region,
    a bottom rim having the inside edge of said bottom rim curved to define a rounded edge,
    said main compression member inside surface defining a frusto-conical surface tapering outwardly from said bottom rim to said top rim, the diameter of said inside surface proximate said bottom rim being greater than the outside diameter of said penis when said penis is engorged,
    means, proximate the bottom rim of said main compression member for holding said cylindrical compression member against said pubic region.

2. The device for maintaining engorgement of said human penis as claimed in claim 1 further comprising
    a generally cylindrical compression member insert comprising,
    a compression member insert inside surface,
    a compression member insert outside surface,
    an insert top rim,
    an insert bottom rim,
    said generally cylindrical insert outside surface defining a frusto-conical surface adapted to engage the frusto-conical inside surface of said generally cylindrical main compression member,
    a detent proximate the outside of said insert bottom rim adapted to engage said rounded edge of said bottom rim of said main compression member.

3. The device for maintaining engorgement of said human penis as claimed in claim 2 wherein said compression member insert comprises
    said insert inside surface diameter is slightly greater than the outside diameter of said penis when said penis is engorged.

4. A device for maintaining engorgement of the human penis as claimed in claim 3 wherein said means proximate the bottom rim of said main compression member for holding said cylindrical compression member against said pubic region comprises
    a pair of connector tabs attached to opposite sides of said main cylindrical compression member proximate the bottom edge thereof,
    a set of holding straps adapted to engage the body of the user, and
    means for attaching said straps to said pair of connector tabs.

5. The device for maintaining engorgement of said human penis as claimed in claim 2 wherein said compression member insert comprises
    said insert inside surface diameter is sufficient to avoid radial compression of said penis that would restrict the flow of blood therethrough.

* * * * *